United States Patent
Wegner et al.

(10) Patent No.: US 11,925,742 B2
(45) Date of Patent: Mar. 12, 2024

(54) CANNULATION TIME TRACKING

(71) Applicant: Fresenius Medical Care Deutschland GmbH, Bad Homburg (DE)

(72) Inventors: Stefan Wegner, Verneck (DE); Reiner Spickermann, Wasserlosen-Burghausen (DE); Klaus Balschat, Schwebheim (DE)

(73) Assignee: Fresenius Medical Care Deutschland GmbH, Bad Homburg (DE)

( * ) Notice: Subject to any disclaimer, the term of this patent is extended or adjusted under 35 U.S.C. 154(b) by 165 days.

(21) Appl. No.: 17/173,011

(22) Filed: Feb. 10, 2021

(65) Prior Publication Data
US 2021/0316059 A1 Oct. 14, 2021

(30) Foreign Application Priority Data
Apr. 10, 2020 (DE) .......................... 102020110112.0

(51) Int. Cl.
*A61M 1/36* (2006.01)

(52) U.S. Cl.
CPC ....... *A61M 1/3661* (2014.02); *A61M 2205/52* (2013.01); *A61M 2205/6072* (2013.01); *A61M 2205/609* (2013.01)

(58) Field of Classification Search
CPC ............ A61M 1/3661; A61M 2205/52; A61M 2205/6072; A61M 2205/609
See application file for complete search history.

(56) References Cited

U.S. PATENT DOCUMENTS

| 5,647,373 | A | 7/1997 | Paltieli |
| 10,507,067 | B2 | 12/2019 | Glozman et al. |
| 2013/0020237 | A1* | 1/2013 | Wilt .................... A61M 1/1654 210/85 |
| 2015/0065916 | A1 | 3/2015 | Maguire et al. |
| 2017/0124284 | A1* | 5/2017 | McCullough ........... A61M 5/20 |
| 2019/0000326 | A1* | 1/2019 | Handler ............... A61B 5/7257 |
| 2019/0374700 | A1* | 12/2019 | Kopperschmidt .. A61M 1/3655 |
| 2020/0069929 | A1* | 3/2020 | Mason ................ A61M 1/3661 |

FOREIGN PATENT DOCUMENTS

| DE | 102010008479 A1 | 8/2011 | |
| DE | 102013002231 A1 | 8/2014 | |
| DE | 10 2013 111 084 A1 | 4/2015 | |
| DE | 102017201440 B3 | 5/2018 | |
| DE | 10 2017 201 437 A1 | 8/2018 | |
| DE | 102017201434 A1 * | 8/2018 | ............. A61B 34/30 |
| DE | 102017201434 A1 | 8/2018 | |

* cited by examiner

Primary Examiner — Lauren P Farrar
(74) Attorney, Agent, or Firm — Leydig, Voit & Mayer, Ltd.

(57) ABSTRACT

A device includes a processor and a non-transitory memory having processor-executable instructions stored thereon. The device is usable with a blood treatment apparatus, such as a hemodialysis machine. The processor-executable instructions, when executed by the processor, facilitate: determining a time point with regard to puncturing a vessel of a patient, wherein puncturing the vessel of the patient is related to a blood treatment for the patient using a blood treatment apparatus; determining a time period based on the determined time point; and transmitting data related to the determined time point and/or data related to the determined time period to a receiving device.

21 Claims, 5 Drawing Sheets

CANNULATION TIME TRACKING

CROSS-REFERENCE TO RELATED APPLICATIONS

Priority is claimed to German Patent Application No. DE 102020110112.0, filed on Apr. 10, 2020, the entire disclosure of which is hereby incorporated by reference herein.

FIELD

The present invention relates to a medical set, a method, a digital storage medium, a computer program product, and a computer program.

BACKGROUND

The extracorporeal blood treatment is known from practice. In this, blood is withdrawn from the patient and led along a blood circuit extracorporeally and, for example, through a blood filter. Prior to the blood treatment, the patient's vessel, usually a fistula or a shunt, is punctured ("cannulated") using cannula(s) and connected to line sections, which in turn may be connected to the extracorporeal blood circuit at the beginning of the blood treatment session using suitable connectors.

The puncture of the patient's vessel is usually carried out in a preparation room, i.e. spatially separated from the blood treatment apparatus by which the planned blood treatment is later carried out.

SUMMARY

In an exemplary embodiment, the present invention provides a device which includes a processor and a non-transitory memory having processor-executable instructions stored thereon. The processor-executable instructions, when executed by the processor, facilitate: determining a time point with regard to puncturing a vessel of a patient, wherein puncturing the vessel of the patient is related to a blood treatment for the patient using a blood treatment apparatus; determining a time period based on the determined time point; and transmitting data related to the determined time point and/or data related to the determined time period to a receiving device.

In another exemplary embodiment, the present invention provides a method. The method includes: determining, by a device, a time point with regard to puncturing a vessel of a patient, wherein puncturing the vessel of the patient is related to a blood treatment for the patient using a blood treatment apparatus; determining, by the device, a time period based on the determined time point; and transmitting, by the device, data related to the determined time point and/or data related to the determined time period to a receiving device In yet another exemplary embodiment, the present invention provides a non-transitory computer-readable medium having processor-executable instructions stored thereon. The processor-executable instructions, when executed, facilitate: determining a time point with regard to puncturing a vessel of a patient, wherein puncturing the vessel of the patient is related to a blood treatment for the patient using a blood treatment apparatus; determining a time period based on the determined time point; and transmitting data related to the determined time point and/or data related to the determined time period to a receiving device.

BRIEF DESCRIPTION OF THE DRAWINGS

The present invention will be described in even greater detail below based on the exemplary figures. The invention is not limited to the exemplary embodiments. All features described and/or illustrated herein can be used alone or combined in different combinations in embodiments of the invention. The features and advantages of various embodiments of the present invention will become apparent by reading the following detailed description with reference to the attached drawings which illustrate the following.

DETAILED DESCRIPTION

Exemplary embodiments of the present invention include a medical set and a method for determining a time point for a puncture.

In addition, exemplary embodiments of the present invention include a digital storage medium, a computer program product and a computer program.

Exemplary embodiments of the present invention include a medical set, a method, a digital storage medium, a computer program product, and a computer program.

In an exemplary embodiment, the present invention relates to a medical set (hereinafter also in short: set), which comprises a user information device and a sending device, wherein the sending device may be part of the user information device or a separate part thereof.

The user information device of the set comprises itself a determining device and an evaluating device, which may be two separate devices or one common device.

The determining device is programmed to determine a time point which is related to the procedure of puncturing a patient's blood vessel, for which patient a blood treatment using a blood treatment apparatus is upcoming or planned in the near future. The determining device is further programmed to transmit this time point to the evaluating device of the user information device. This may be done in a wired or wireless manner or in a different manner.

The evaluating device is programmed to optionally transmit the determined time point and/or the information related to the determined time point to the sending device of the medical set. Alternatively or additionally, it is programmed to determine a time period starting from or based on the determined time point and to transmit information related to this determined time period to the sending device.

The sending device of the medical set according to the present invention is programmed to receive this information. It is further programmed to transmit a signal related to a time point or time period, specified herein, to at least one receiving device which may be part of the set or separate thereof.

A method according to the present invention for determining a time point or a time period related to the puncture of a vessel (or to the moment of puncture) of a patient for the purpose of a blood treatment which is upcoming or planned using the blood treatment apparatus, encompasses the step of providing a medical set according to the present invention.

Furthermore, a method according to the present invention encompasses at least one of the following steps:
a. entering the time point of a completed puncture of a patient's vessel by the user; and/or
b. authenticating the user and/or the patient at or by the user information device; and/or
c. entering and/or specifying the time point, using the user information device, at which the blood treatment apparatus is (again) ready to start a/the next blood treatment, wherein the time point is entered by the user or specified by the control device or closed-loop control device of the blood treatment apparatus.

As a further optional step, the user information device may, based on the information entered or transmitted in step a. and/or in step c., calculate all further times points and/or time periods mentioned herein and then transmit them to a device designated thereto in order to output them and/or for further processing.

Whenever a method step is mentioned herein, the present invention also encompasses a corresponding programming or a configuration of a suitable device or of a section thereof, in particular for executing the relevant method step.

It will be appreciated that the execution of the various machine-implemented processes and steps described herein may occur via the execution, by one or more respective processors, of processor-executable instructions stored on a tangible, non-transitory computer-readable medium, such as random access memory (RAM), read-only memory (ROM), programmable read-only memory (PROM), and/or another electronic memory mechanism. Thus, for example, operations performed by a medical device or another device as discussed herein may be carried out according to instructions stored on and/or applications installed on one or more respective computing devices. Examples of non-volatile computer-readable storage mediums include a floppy disk, memory card, CD, DVD, EPROM, FRAM (Ferroelectric RAM) or SSD (Solid State Drive). A memory, with electronically or optically readable control signals, can interact with a programmable hand-held and/or mobile receiver/sender of the user or of the patient, in particular its programmable computer system, such that said programmable receiver/sender is programmed or reprogrammed to be a user information device of a medical set according to the present invention.

The computer program product according to the present invention comprises a program code saved on a machine-readable memory for prompting the programming or reprogramming of a programmable hand-held and/or mobile receiver/sender of the user or of the patient, which may for example be a smartphone, tablet, laptop or the like, to be a user information device of a medical set according to the present invention, when the computer program product runs on a computer.

A computer program product may according to the present invention be understood as, for example, a computer program which is stored on a memory, an embedded system as a comprehensive system with a computer program (for example, an electronic device with a computer program), a network of computer-implemented computer programs (for example, a client-server system, a cloud computing system, etc.) or a computer on which a computer program is loaded, running, saved, executed or developed.

The term "machine-readable memory" as used herein, refers in certain embodiments of the present invention to a memory, which contains data or information interpretable by software and/or hardware. The memory may, for example, be a diskette, a CD, DVD, a USB stick, a flashcard, an SD card or the like, as well as any other memory or any other storage medium mentioned herein, respectively.

A computer program according to the present invention encompasses a program code by which a programmable hand-held and/or mobile receiver/sender of the user of the patient is programmed or reprogrammed to be a user information device of a medical set according to the present invention, when the computer program runs on a computer.

Embodiments according to the present invention may comprise one, several or all of the following features in any combination, unless indicated otherwise or contradicted by context. Advantageous developments of the present invention are each also subject-matter of the dependent claims.

Whenever numerical words are mentioned herein, the person skilled in the art shall recognize or understand them as indications of numerical lower limits. Unless it leads the person skilled in the art to an evident contradiction, the person skilled in the art shall comprehend for example the specification of "one" as encompassing "at least one". This understanding is also equally encompassed by the present invention as the interpretation that a numerical word, for example, "one" may alternatively mean "exactly one", wherever this is evidently technically possible for the person skilled in the art. Both are encompassed by the present invention and apply to all numerical words used herein.

Whenever an embodiment is mentioned herein, it is an exemplary embodiment according to the present invention.

In several embodiments, the medical set comprises a blood treatment apparatus with a control device or closed-loop control device, by which a blood treatment of the patient using the blood treatment apparatus may be controlled or regulated.

In some embodiments, the receiving device is a portable device, for example a hand-held and/or mobile receiver/sender, which may herein be e.g. a smartphone.

The receiving device may be accessible to the patient or to a user who is for example a nurse or a doctor. Optionally, both the patient and the user have access to a receiving device each.

The receiving device may optionally be a monitor, display, tablet or other hand-held device such as a Personal Digital Assistant (PDA), beeper, smartphone or the like.

The receiving device may serve to provide information, e.g. to be noted by the user or by the patient, for example in the form of an input/output device or of a display of the user information device.

In certain embodiments, the control device or closed-loop control device of the blood treatment apparatus may be the receiving device, comprise it or map or take over its function.

In some embodiments, the determined time point indicates a point in time when the (blood) vessel, e.g. the shunt, of the patient was punctured.

In several embodiments, the evaluating device is programmed to specify a time period that elapsed since the patient has been punctured.

In some embodiments, the evaluating device is programmed to specify the time point that corresponds to the end of a time period specified as being the maximum permissible, after which connecting the patient to the blood treatment apparatus or starting the blood treatment session is not possible and/or recommendable without further measures relating to the punctured vessel for not endangering the patient's well-being.

The time period that is specified as the maximum permissible may be regarded as a period in which blood clotting in the cannulas and line sections, to which the patient is connected via a puncture prior to an upcoming blood treatment session, can be excluded according to predetermined criteria.

In several embodiments, the determined time point is a future time point at which the blood treatment apparatus is, based on predetermined criteria or based on the experience of the user, likely ready or ready again to start a new blood treatment session. It is known that the preparation of a blood treatment session takes some time, the so-called preparation or equipping time (removing or inserting disposables, disinfecting, rinsing, priming, reading patient data and the like). The determined time point of these embodiments, if communicated early, may help to puncture the patient not too early, but also not too late.

In several embodiments, the determined time point is a future time point at which the patient may as early as possible or as late as possible be connected to the blood treatment apparatus for undergoing a blood treatment.

Using the evaluating device, a suitable time point or time period for puncturing the patient may then be determined starting from the time point determined in this way. Specifying this time point/time period is preferably carried out according to certain criteria.

Alternatively or additionally, the evaluating device may be used to determine a time point corresponding to the beginning of the time period specified as being the maximum permissible. The beginning of the time period specified as being the maximum permissible defines the earliest possible time point for puncturing the patient. The time period specified as being the maximum permissible may lie in the future and may be defined by its start and/or by its end or by these points. It may be understood herein as the time period within which the patient should be punctured in order to ensure that blood—which flows from the puncture into the cannulas connected to his vascular system and into the line sections that extend from them, but then remains there (i.e. no longer flows) until these line sections are connected to the blood tubing set or to the blood treatment apparatus—will not clot, and therefore the patient may be connected at a later time point to the extracorporeal blood circuit of the blood treatment apparatus by the connectors of the line sections without risk of blood clots.

In some embodiments, the start of the blood treatment corresponds to the completed connection of the patient's vascular system to the extracorporeal blood circuit of the blood treatment apparatus, for example by a connector provided for this purpose.

In some embodiments, the predetermined criteria encompass or take into account the history of the specific patient. In this, the history encompasses for example the average time between cannulation and the start of treatment, which was recorded and averaged e.g. over several treatment sessions. Amongst others, typical behavioral patterns of the patient may be detected (movement speed, orientation, toilet use, etc.). Conversely, the average time may give an indication of when the patient, freshly cannulated in the preparation room, will most likely—or on the basis of experience with the specific patient under identical or comparable circumstances—reach e.g. the treatment room. By using the evaluating device, it is thus possible to determine a suitable time point or time period for puncturing the patient, for example based on the time point determined as disclosed herein, which also takes into account the patient's history.

The history of the patient may therefore preferably be taken into account when determining the specific criteria.

In several embodiments, the user information device of the medical set, in particular its input/output device, may be programmed such that the determined time point may be manually entered into it. The manual input is preferably done by a user.

In several embodiments, the time point referred to herein as the determined time point is determined by the medical set (without human intervention), in particular by the determining device of the user information device.

In some embodiments, the medical set or its user information device is or comprises a hand-held and/or mobile receiver/sender. The mobile receiver/sender may be assigned to the user and/or to the patient, i.e. the user and/or the patient may each carry it with them.

In several embodiments, the receiver/sender is configured to only receive signals, in other embodiments it is configured to only send signals. In some embodiments, the receiver/sender is configured to send and receive signals.

In several embodiments, the determining device of the set is configured and/or programmed to automatically determine the time point at which the patient's vessel was punctured.

For this purpose, sensor arrangements, e.g. optical sensors, cameras or the like, and one or more time detecting device(s) associated with them, e.g. in the form of a clock, may be provided.

In some embodiments, the medical set encompasses an identification device. The identification device may be programmed or configured to link information on the determined time point and/or specified time period with information on the identity of the punctured patient, e.g. in a data set. The identification device may be part of the user information device or may be separate thereof.

In several embodiments, the identification device is programmed or configured to capture a QR code (Quick Response) or the like. Alternatively or in addition, the identification device may be programmed to capture biometric data, i.e. it is for example provided to read a fingerprint, perform an iris scan, facial recognition or the like.

In some embodiments, the identification device is programmed or configured to anonymously associate identity information with the determined time point or the specified time period.

This may for example be done by having the patient wear a bracelet with a unique QR code. The user may scan this code, e.g. after a completed puncture, which would link the time point of the puncture to the QR code, but not necessarily to the patient's real name. The patient may then be identified again at the blood treatment apparatus by rescanning the QR code. The determined time point may thus be assigned to the specific patient error free.

A radio frequency identification tag (RFID tag) may also be provided in certain embodiments together with a suitable sensor arrangement for the identification.

In several embodiments of the medical set, the user information device, its determining device and/or the identification device are programmed or configured to allow data entry or data manipulation, i.e. changing or deleting the corresponding values, in particular the information concerning the determined time point, the determined time period, the time period specified as being the maximum permissible and/or the like, only after the user and/or patient have been authenticated.

In several embodiments of the medical set, the user information device is part of the blood treatment apparatus.

In some embodiments of the medical set, the control device or closed-loop control device of the blood treatment apparatus is programmed or configured to block, at least temporarily, the execution of at least one function of the blood treatment apparatus upon receipt of the signal from the sending device. In this, blocking occurs particularly when the duration of the specified time period between the determined time point and the current time exceeds the duration of the time period specified as being the maximum permissible, which may be represented by the signal.

In certain embodiments, the blood treatment apparatus and/or the receiver/sender of the user or of the patient are programmed to indicate a recommendation for or against a blood treatment upon the reception of the signal from the sending device. This may be done on an optical indicator, e.g. a display, but also as a pure color signal, e.g. by LEDs that switch from green to red, for example, if the signal from the sending device indicates that the time period specified as being the maximum permissible has been exceeded.

Alternatively or additionally, these devices may be programmed to indicate or to request for actions possibly to be taken, such as a flushing or a re-cannulation.

In several embodiments, the blood treatment apparatus may be a dialysis apparatus, hemodialysis apparatus, hemofiltration apparatus or hemodiafiltration apparatus, in particular as an apparatus for acute renal replacement therapy, for chronic renal replacement therapy or for continuous renal replacement therapy (CRRT).

In some embodiments, the medical set is or comprises a portable device.

In some embodiments, the medical set or a part thereof, for example the user information device, is in a data-related connection to a central or distributed processing unit, for example via WLAN, WiFi, Bluetooth, Near Field Communication (NFC), mobile radio (communications), etc.

In some embodiments, the medical set is or encompasses a personal smartphone of the patient, which is programmed for the above-mentioned tasks. A corresponding software application ("App") can use the functionality provided by this device for authentication (unlocking the screen by fingerprint sensor, camera, PIN code, password, entering a pattern and the like) to unambiguously identify the patient and optionally also the user, i.e. the attending healthcare professional, or to verify their authorization. After authentication, the relevant functionalities of the application may be accessible or enabled, for example the option of manually entering the puncture time as the determined time point.

In some embodiments, the control device or closed-loop control device of the blood treatment apparatus is programmed to initiate or trigger itself (e.g. by giving instructions to the user), to monitor, control or closed-loop control the equipping of the blood treatment apparatus prior to a blood treatment and (as well as) the blood treatment or steps thereof. Since the blood treatment apparatus may thus have knowledge of the time remaining, e.g. until the end of the current blood treatment session, until the completion of equipping said blood treatment apparatus for the next treatment session, until a possible start of the blood treatment session of the next patient, etc., it may, e.g. through appropriate programming as mentioned above, give a corresponding indication (or signal) at the appropriate time when it will be ready for the following treatment session, or when the vessel of the next patient should ideally be punctured.

In some embodiments, the location of the patient within the treatment rooms (preparation room, waiting area, treatment room) may be tracked and thus the patient's identity may be verified, for example, by a Real Time Location System (RTLS) programmed to detect the proximity of the patient to specific devices, in particular to dedicated sensor arrangements and/or to the blood treatment apparatus. This continuous tracking may be used to determine the patient-related time points, for example to determine the time point of puncture and the time point of his appearance at the blood treatment apparatus assigned to him/her for the blood treatment.

For this purpose, in certain embodiments, the data of the clinic's treatment plan for the corresponding day is used for processing e.g. by the network or the IT system of the clinic, which may advantageously lead to an optimized sequence of successive or parallel blood treatment sessions. Therefore, it is provided in some embodiments to adapt or optimize existing treatment schedules based on the determined patient-related times points. If, for example, it is foreseeable that a concretely considered patient will arrive at a blood treatment apparatus later than noted for him/her in the treatment schedule, given the time of his/her cannulation, then a current treatment, i.e. a treatment currently performed and still running using this treatment apparatus, may last longer in favor of the currently treated patient than originally set in the treatment schedule (for example, due to changed settings on the blood treatment apparatus, which may affect the currently still running treatment session). Conversely, if the patient in question is cannulated too early, an ongoing treatment session of the patient currently being treated—if suitable—may be shortened or brought to an early end (for example by increasing the blood and/or dialysate flow or by increasing the ultrafiltration rate). Thus, the patient punctured too early, may be treated without a longer waiting period, if applicable, and thus without the risk of a mandatory re-puncturing. For this purpose, the patient who is treated in an "accelerated" manner may either be discharged with an unattained treatment goal (kT/V or ultrafiltration volume) if medically justifiable, which will be compensated by a subsequent blood treatment session, or said patient may reach the treatment goal more quickly by a change in the therapy parameters (see above). This is also done under consideration of medical expertise, if necessary, supported by physiological measurements. In several embodiments, the determined time point may thus influence the treatment session of at least one patient. The medical set may be provided or programmed accordingly.

Some or all of the embodiments according to the present invention may comprise one, several or all of the advantages mentioned supra or in the following.

The length of the time period between puncture and the start of the blood treatment session is influenced by a variety of events. Such events may include, for example, delays by a patient who has been treated immediately before at the same blood treatment apparatus, delays in carrying out hygienic measures, delays by the patient himself, for example due to reduced or restricted mobility, going to the toilet or personal discomfort. Lack of personnel is also a common reason for such delays.

If the duration of this time period between puncture and start of treatment (e.g. the first detection of blood by an optical sensor, the first conveyance of blood by the blood pump, the first return of treated blood to the patient) exceeds a limit value, coagulation of the blood in the cannula(s) or in the line sections connected to them is possible, which makes further measures necessary before the upcoming blood treatment of the patient may actually be started.

Since a possible coagulation is not necessarily visible to the naked eye, the question arises for the treating healthcare professionals, referred to herein as user, whether an already punctured patient may still be connected to the extracorporeal blood circuit of the blood treatment apparatus at a given time. This question may advantageously be answered by the present invention.

For example, by detecting the time period that has elapsed since the puncture of the patient's vessel and due to the fact that this time period is known to the user of the blood treatment apparatus, the present invention can ensure based on experience that at the time point of the start of the blood treatment using the blood treatment apparatus, blood coagulation in the cannulas and the connected line sections has in all probability not yet taken place. Otherwise, the cannula may be replaced and/or rinsed, optionally prompted by a message from the medical set, optionally even prior to the blood treatment session, which would have to be stopped or interrupted in the event of late detection of coagulation. Thus, according to the present invention this not only may increase the patient safety, but may also make the time required for the upcoming blood treatment session predictable.

By the present invention, patient-related histories, for example with regard to the blood coagulation time and thus indirectly for the time period specified as being the maximum permissible, and/or statistical evaluations, for example with regard to the reasons for delays that have occurred, may be created using the determined data. Furthermore, data may be collected regarding the equipping times (and/or removing times) of the blood treatment apparatus(es), patient waiting times between puncturing and treatment, or the like. As a result, better utilization of the blood treatment apparatuses may be achieved, which in turn may advantageously result in shorter waiting times for the patients.

Another advantage is that time may be saved by involving the patient using the receiver/sender assigned to him, e.g. his smartphone, wherein the patient, when he receives a notification, for example on his smartphone, may, if necessary, for example when a time period specified as being the maximum permissible was exceeded, contact a healthcare professional for a new puncture already before changing rooms and/or before going to the blood treatment apparatus.

All advantages achievable with methods according to the present invention may also be achieved undiminished with apparatuses according to the present invention, and vice versa.

Figure 1:
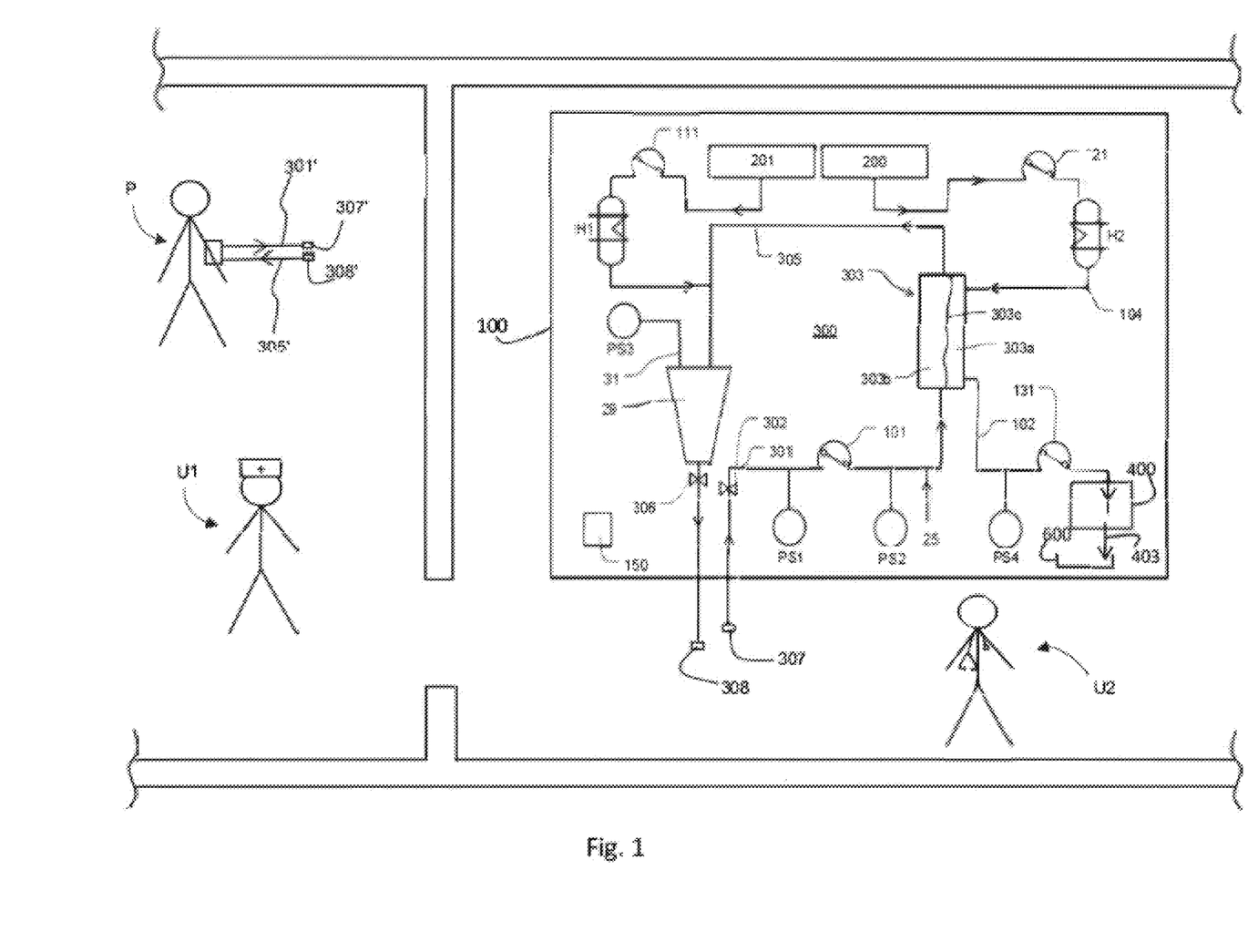
FIG. 1 shows a simplified representation of a blood treatment apparatus as an optional component of a first embodiment of a medical set.

FIG. 1 shows a simplified representation of a blood treatment apparatus 100 as an optional component of a first embodiment of a medical set according to the present invention.

FIG. 1 shows a simplified representation of a process flow diagram of a blood treatment apparatus 100 according to the present invention, optionally connected to an extracorporeal blood circuit 300 and a discharge hose system which leads to an optional effluent bag 400.

The extracorporeal blood circuit 300 comprises a first line 301, here an arterial line section.

The first line 301 is in fluid communication with a blood treatment device, here exemplarily a blood filter or dialyzer 303. The blood filter 303 comprises a dialysis liquid chamber 303a, through which dialysis liquid is guided during use, and a blood chamber 303b, through which blood is guided during use. The dialysis chamber 303a and the blood chamber 303b are mostly separated from each other by a semipermeable membrane 303c. Blood and dialysis liquid are usually passed through the blood filter 303 in the countercurrent principle. The blood is purified in the blood filter 303.

The extracorporeal blood circuit 300 further comprises at least a second line 305, here a venous line section.

Both the first line 301 as well as the second line 305, serve as their connection to the vascular system of the patient P (in FIG. 1 on the left). For this purpose, a connector 307 is provided at the open end of the first line 301 and a connector 308 is provided at the open end of the second line 305. Corresponding connectors 307' and 308' are respectively provided on the open ends of the lines leading to the vascular system of the patient P for connecting the patient P or his vascular system to the extracorporeal blood circuit 300.

The first line 301 is optionally connected with a (first) hose clamp 302 for blocking or closing the line 301. The second line 305 is optionally connected to a (second) hose clamp 306 for blocking or closing the line 305.

The blood treatment apparatus 100 which is represented in FIG. 1 only by some of its devices and merely schematically, comprises a blood pump 101. During the patient's treatment, the blood pump 101 conveys blood through sections of the extracorporeal blood circuit 300 towards the blood filter or dialyzer 303. This is illustrated by the small arrows, which generally indicate the flow direction in each of the figures.

Fresh dialysis liquid is pumped from a source 200 along the dialysis liquid inlet line 104 into the dialysis liquid chamber 303a, by a pump for dialysis liquid 121, which may be configured as a roller pump or as an otherwise occluding pump. The dialysis liquid leaves the dialysis liquid chamber 303a towards the effluent bag 400 as dialysate, possibly enriched with filtrate. The filtrate may comprise water which was withdrawn from the blood in the blood filter. Filtrate and dialysate will be referred to herein individually or collectively simply as effluent.

In practice, the effluent is immediately discarded by a dialysate outlet line 102 or, especially in acute treatment, is fed to the effluent bag 400 and initially stored in it. After completion of the blood treatment, or in bag emptying intervals during the blood treatment (intervals in which the effluent bag 400 is emptied), the effluent is discarded out of the effluent bag 400, by a discharge line 403, e.g. into a sink or a differently designed basin 600.

The source 200 may be, for example a bag or a container. The source 200 may also be a fluid line through which on-line and/or continuously generated or mixed liquid is provided, for example a hydraulic outlet or hydraulic connection port of the blood treatment apparatus 100.

A further source 201 with substitute may be optionally provided. It may correspond to the source 200 or be a separate source.

In addition to the aforementioned blood pump 101, the arrangement shown in FIG. 1 further comprises purely optionally a series of further pumps, in each case optional, namely the pump 111 for substitute, the pump 121 for dialysis liquid and the pump 131 for the effluent.

The optional pump 111 is provided to supply the second line 305 with substitute from the optional source 201, for example out of a bag, and via an optionally present bag heater H1 with a heating bag.

The pump 121 is provided to supply the blood filter 303, using a dialysis liquid inlet line 104, with dialysis liquid from a source 200, for example out of a bag, via an optionally present bag heater H2 with a heating bag.

The dialysis liquid, thus supplied, exits again from the blood filter 303 via a dialysate outlet line 102 supported by the optional pump 131, and may be discarded.

Upstream of the blood pump 101, an optional arterial sensor PS1 is provided. During a patient's treatment it measures the pressure in the arterial line.

Downstream of the blood pump 101, but upstream of the blood filter 303 and if provided, upstream of an addition site 25 for heparin, a further optional pressure sensor PS2 is provided. It measures the pressure upstream of the blood filter 303 ("pre-hemofilter").

Again, a further pressure sensor to measure the filtrate pressure of the blood filter 303 may be provided as PS4 downstream of the blood filter 303, however preferably upstream of the pump 131 in the dialysate outlet line 102.

Blood, which leaves the blood filter 303, passes through an optional venous blood chamber 29, which may comprise a de-aeration device 31 and/or a further pressure sensor PS3. The blood is then returned to the patient (reinfused).

A control device or closed-loop control device 150 may be configured to control the blood treatment apparatus 100 for the purpose of a blood treatment session. In this example, it is part of the blood treatment apparatus 100. In some embodiments the control device or closed-loop control device 150 may be provided separate from the blood treatment apparatus 100.

The control device or closed-loop control device 150 may be in cable or wireless signal communication to any of the components of the medical set.

FIG. 1 also shows two users U1 or U2. They may be medical care or nursing staff or a doctor. In the embodiment shown in FIG. 1, user U1 is involved in the preparation of the blood treatment, for example by puncturing the vessel of the patient P in preparation for the blood treatment, e.g. in a preparation room, i.e. for example a room (outlined on the left in FIG. 1) separated from than the treatment room (outlined on the right in FIG. 1), in which the treatment will take place.

Figure 2:
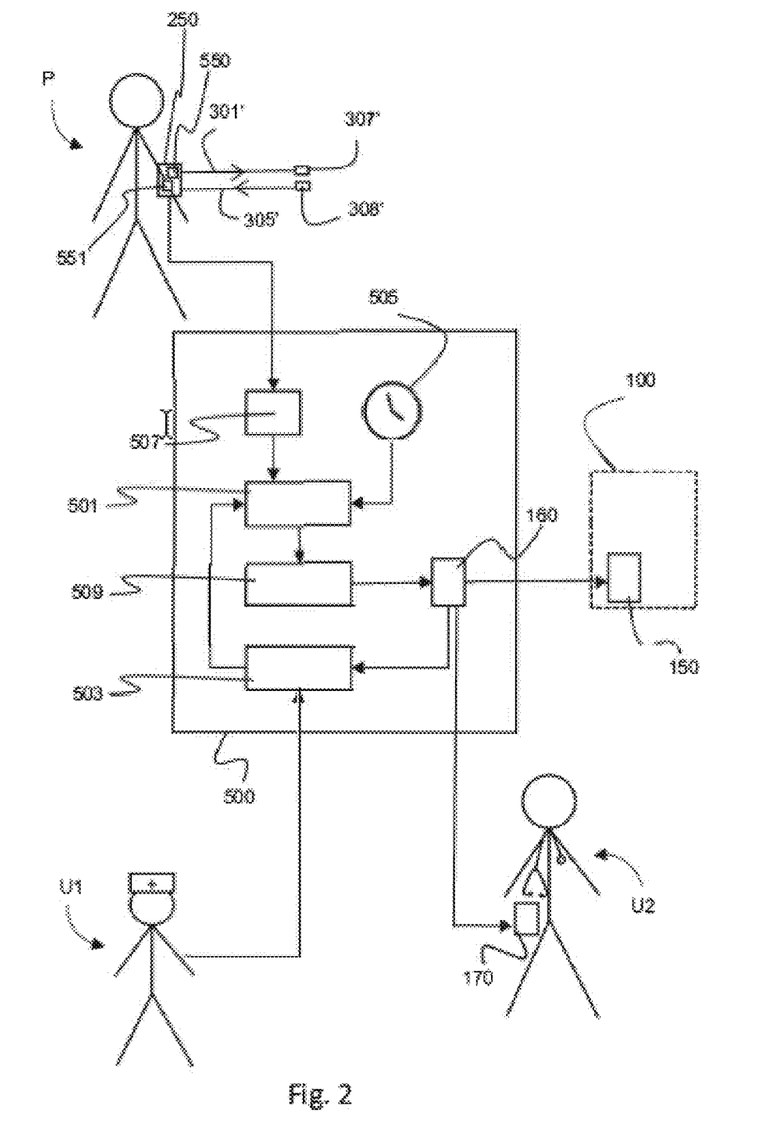
FIG. 2 shows a simplified representation of a medical set according to a second embodiment.

FIG. 2 shows a simplified representation of a medical set according to the present invention in a first embodiment. The blood treatment apparatus 100, which is optionally included in the set, is here, in contrast to FIG. 1, only outlined schematically.

A user information device 500 of the set, which may exemplarily be or encompass the smartphone of patient P, comprises in the embodiment of FIG. 2, each of which being optional, an identification device 507, a determining device 501, an evaluating device 509, an input/output device 503 for inputting and/or outputting information, a time recording device 505 and/or a sending device 160.

The determining device 501 serves the user information device 500 to determine the time point $t_P$ at which the patient's vessel P has been punctured (also: cannulated). For this purpose, a variety of designs and possible uses of the determining device 501 are contemplated by the present invention. Some of these embodiments are described in the following with regard to FIG. 2.

For example, the determining device 501 may be configured to record, preferably automatically, the puncturing of the vessel of patient P which has been carried out and therewith to determine and/or store the time point $t_p$ (see FIG. 3) at which the puncturing was made, preferably also automatically.

The detection may be done, for example using sensors of the user information device 500 or by other devices of the medical set. They may be provided, for example in or on the stretcher or chair on which the patient P usually sits for the puncture of his vessel, or for monitoring them. Suitable sensors may react or respond to pressure or pressure changes (e.g. caused by changes in weight on the patient couch or chair caused by the patient P who sat down), to heat radiation from patient P in the immediate vicinity of the patient couch or chair, etc. Suitable sensors may be optical sensors, such as cameras, which may detect the presence of the patient P, e.g. on the stretcher or chair. When using such or other sensors, the time point $t_P$ may be determined in a first, but sufficient, approximation, for example, as the time at which the patient P e.g. lies down on the stretcher or sits on the chair or leaves it/them again.

Automatic detection may also be carried out by an optional sensor 551, which is present at a fistula or puncture site 250 of patient P. The sensor 551 may be an optical sensor which checks whether blood is present in the line sections 301', 305'. However, it may also be another sensor which may detect that a puncture has taken place, for example a pressure sensor. The sensor 551 in this case is exemplarily present in, or comprises, a puncture sending device 550, likewise optional, which may send the message about a successful puncture to the user information device 500 or its determining device 501. The corresponding transmission may be wireless, for example or via NFC, RFID or Bluetooth, or other wireless methods or via wired methods.

The above-mentioned sensor 551 may be part of a cannulation robot for the automatic and/or mechanical puncture of a vessel of the patient P. Such a robot is optionally part of the medical set. Examples are described in U.S. Patent Publication No. 2019/0374700 A1, U.S. Pat. No. 5,647,373, U.S. Patent Publication No. 2015/0065916 A1, and U.S. Pat. No. 10,507,067, the disclosures of which are incorporated herein by reference.

In order to determine the time point $t_P$ using the determining device 501 as described above, it may be in signal communication with the optional time recording device 505. The time recording device 505 may be, or may comprise, a clock and/or it may be provided to be in signal communication with an external clock, for example a network clock, a ward clock or an atomic clock.

In addition to or as an alternative to the automatic determination of the time point $t_P$ at which the puncture has taken place or is considered to have taken place, the determining device 501 may be informed by manual input by the user U1 on the input/output device 503 that the patient P has been punctured at time point $t_P$. Thus, it may be provided that the user U1 actively enters the time point $t_P$ into the input/output device 503 which is configured as a touch screen, keyboard input or the like and which may be, for example, the touch screen or the display of a smartphone of the patient P. The determining device 501 may be programmed to read in or to import the time point $t_P$ entered in this way.

The time point $t_P$ is transmitted from the determining device 501 to the evaluating device 509.

The evaluating device 509 serves the user information device 500 to transmit the time point $t_P$ and/or further information based on the time point $t_P$ to the sending device 160 so that it may be sent by the latter to one or more receiving devices as described below.

Information based on the time point $t_P$ may include the end time point t2 of a time period $T_{max}$ determined by the set or by user U1 as being the maximum permissible, or further information on time points determined by the set or the user U1 based on such time period $T_{max}$.

The time period referred to herein as $T_{max}$ is determined by the time span between two points in time point t1 and t2 (see also FIG. 3), wherein the time point t1 is the time point from which patient's blood is present for the first time in the cannulas or line sections 301' and 305', while the time point t2 is the time point from which blood clotting in the line sections 301' and 305' is expected to occur. The length of the period $T_{max}$ may be known from empirical values, look-up table(s), etc., which may preferably be shortened by a safety time buffer. Thus, the end of the period $T_{max}$ advantageously indicates the time point up to which no blood clotting is to be expected in the cannulas or in the line sections 301' or 305'.

If a patient is punctured at the time point $t_P$, then $t_P=t1$, because blood is present for the first time in the cannulas or the line sections 301' or 305' from the time point $t_P$ of the puncture.

The information generated by the evaluating device 509 may consist of or comprise, for example, the end of the time period $T_{max}$, i.e. the time point t2, since this corresponds to the time after which a blood treatment may no longer be started without further action, without possibly endangering the well-being of the patient.

The information may relate to a time period T which lies between the time point $t_P$ of the puncture and a current time, and to the information whether the duration of the time period T is less than the duration of the time period $T_{max}$, i.e. $T \leq T_{max}$ applies, i.e. whether a blood treatment could still be started at the current time without concerns about blood clotting.

The information generated by the evaluation device 509 may optionally encompass information on the identity of the patient P and/or for his authentication. Alternatively or in addition, information on the authentication of the user U1 or U2 may optionally be included according to the present invention.

The identity of the patient P may be verified using the identification device 507. Identity-related information may be linked to information on the determined time point $t_P$ or information that has been determined or calculated based thereon. In this way it may be ensured that a time point $t_P$ is not inadvertently assigned to a patient other than the patient P who was actually punctured or still to be punctured at the time point $t_P$.

A comparatively simple way of identification is for example the patient P unlocking his/her smartphone in case the smartphone is used as a user information device 500 or as part of it, since it may be assumed that such unlocking cannot be prompted or initiated by any other patient in the hospital than the patient P.

In this, identity information may be made anonymous, for example by assigning a QR code, a fingerprint or the like.

As mentioned above, the information generated by the evaluating device 509 is transmitted to the sending device 160.

The sending device 160 is configured to send or pass on the information it has received from the evaluating device 509 to a receiving device, for example the input/output device 503, for example a display of the user information device 500, and/or to at least one receiver/sender 170 of the user U1 or U2, for example his smartphone, beeper or tablet, for informing the latter and/or to the control device or closed-loop control device 150 or another device of the blood treatment apparatus 100.

The control device or closed-loop control device 150 or the other device of the blood treatment apparatus 100 may be configured to receive the above-mentioned information from the sending device 160, in particular the point of time point $t_P$ of the puncturing the patient P, preferably additionally information about the identity of the patient P.

The control device or closed-loop control device 150 may also be programmed to recognize that the patient P is to be connected to the blood treatment apparatus 100 for starting the blood treatment, which may be possible, for example, on the basis of the identity information transmitted to it. The time at which the patient's treatment session is to begin is herein referred to as time point $t_B$.

The blood treatment apparatus 100 or its control device or closed-loop control device 150 may be programmed in various ways to recognize that patient P is now awaiting blood treatment by the blood treatment apparatus 100. A simple way for this is the user U2 entering personal data of the patient P such as his name, insurance data, previous treatment settings, etc. in the blood treatment apparatus 100 or have the latter read in said information, for example from a patient card.

Alternatively, it may be provided that the blood treatment apparatus 100 or its control device or closed-loop control device 150 is programmed to recognize the proximity of the punctured patient P and to determine or specify the time of this recognition as the time point $t_B$ at which the start of the blood treatment session is imminent and to transmit this information to the evaluating device 509. Said recognition is done, for example, by sensors, e.g. motion sensors and/or a camera.

By transmitting the time point $t_B$, the evaluating device 509 is enabled to set the times $t_P$ and $t_B$ of the specific patient P in relation to each other and to evaluate whether the time point $t_B$ is still within the period $T_{max}$, i.e. whether $t1 \leq t_B \leq t2$ applies.

Alternatively, the evaluating device 509 may determine the time period T which has elapsed between the time point $t_P$ of the puncture and the time point $t_B$ (as current time) and whether the duration of the time period T is still less than the duration of the time period $T_{max}$ which is defined as being the maximum permissible ($T \leq T_{max}$).

The evaluating device 509 is programmed to transmit the result of its evaluation to the sending device 160, which in turn transmits this evaluation and/or the consequence of this evaluation to at least one receiver/sender 170 of the user (U1, U2) and/or of the patient P and/or to the control device or closed-loop control device 150 of the blood treatment apparatus 100. In the simplest case, the consequence of the evaluation is a go signal or a stop signal for informing the user (U1, U2) or towards the control device or closed-loop control device 150.

If the time point $t_B$ is within the time period $T_{max}$ defined as the maximum permissible or if the duration of the time period T is less than the duration of the time period $T_{max}$, the patient P may, without any concern about blood clotting already occurring in the line sections 301', 305', be connected to the lines 301, 305 of the extracorporeal blood circuit 300, using the corresponding connectors 307', 308', for the purpose of blood treatment and the control device or closed-loop control device 150 may initiate, for the blood treatment.

However, if the time point $t_B$ is after the time point t2, i.e. after the end of the period $T_{max}$ (i.e. $t_B > t2$), which is defined as the maximum permissible time, or if the duration of the time period T is longer than the duration of the period $T_{max}$ (i.e. $T > T_{max}$), it may be determined that a blood treatment using the blood treatment apparatus 100 is not allowed, since blood clotting in the cannulas or in line sections 301', 305' of patient P cannot be excluded. In this case, the control device or closed-loop control device 150 can block the blood treatment of patient P.

Alternatively or in addition, the control device or closed-loop control device 150 may be used to indicate what action should be taken before the start of the planned blood treatment session, e.g. whether patient P should be punctured again, whether the cannula(s) and line sections 301', 305' should be flushed or the like.

As shown above, the evaluating device 509 is connected downstream of the determining device 501 and may determine and/or add further information in addition to the data transmitted to it by the determining device 501. In some embodiments however, the latter is not the case, rather the function of the evaluating device 509 is limited to merely forwarding results of the determining device 501. Particularly in such cases, evaluating device 509 and determining device 501 may be configured in one common device. In other embodiments, evaluating device 509 and determining device 501 are configured as separate devices.

Figure 3:
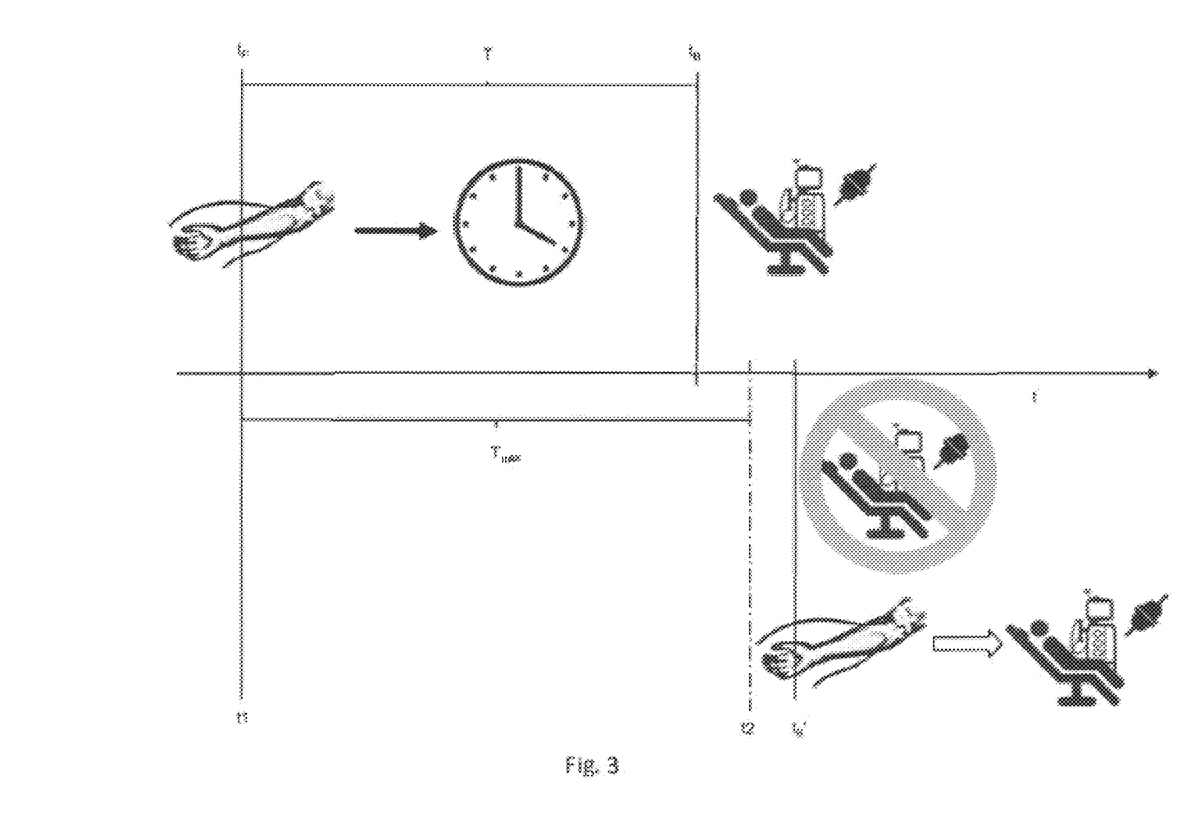
FIG. 3 shows a simplified representation of a chronological sequence of a method according to a first embodiment.

FIG. 3 shows in a simplified representation the chronological sequence of the method according to the present invention in a first embodiment.

The vessel or vessels of the patient P are punctured, and the time point $t_P$ at which this takes place or is considered to have taken place is determined by the determining device 501 (see FIG. 2). This may be done automatically, for example by optical sensors or cameras, or by the user U1 manually entering the corresponding time point $t_P$ of the puncture, for example via the input/output device 503 of the user information device 500, or the like.

Based on this time point $t_P$, which here is equal to the time point t1, i.e. the beginning of the period $T_{max}$ specified as being the maximum permissible, the end of the period $T_{max}$, namely the time point t2, may be determined. In this, it is assumed that no blood clotting should have occurred within the time period $T_{max}$ within the cannula(s) and line sections 301', 305' (see FIG. 1 and FIG. 2). Since this can no longer be guaranteed after the end of this period, i.e. after time point t2, blood treatment should not be started with relevant the patient P after time point t2 for reasons of patient safety.

Before the patient P is connected to the blood treatment apparatus 100 for undergoing a blood treatment, the time point $t_B$ at which the patient P moves towards the vicinity of the blood treatment apparatus 100, the patient is to be connected to the blood treatment apparatus 100 or the treatment is to begin is recorded analogous as described to FIG. 2. This time point is designated in FIG. 3 as $t_B$ for a first case and $t_B'$ for a second case.

In the example of time point $t_B$, this time is still within the time period $T_{max}$ previously specified as being the maximum permissible (see FIG. 3 above), i.e. before its end. Accordingly, the control device or closed-loop control device 150 may trigger the blood treatment apparatus 100 to initiate the blood treatment for the patient P due to the reasons mentioned above. This is represented in FIG. 3 above by the representation of a patient on a treatment couch after the time point $t_B$.

In the example at the bottom of FIG. 3, the time point $t_B'$, which was determined e.g. by the user U2 or by the control device or closed-loop control device 150, is beyond the time period $T_{max}$ (see FIG. 3 below), which was previously specified as being the maximum permissible, i.e. after its end t2. Accordingly, the control device or closed-loop control device 150 in this embodiment will block the blood treatment apparatus 100, e.g. in such a way that no blood treatment can be started, or the user U2 refrains from connecting the patient to the blood treatment apparatus 100 without further measures. In this case, the patient P, is for example first punctured again or the line sections 301', 305' are flushed to avoid any complications during the blood treatment. This procedure is represented in FIG. 3 at the bottom after the time point $t_B'$ by the arm being cannulated again and the (possibly) subsequent start of a blood treatment.

Figure 4:
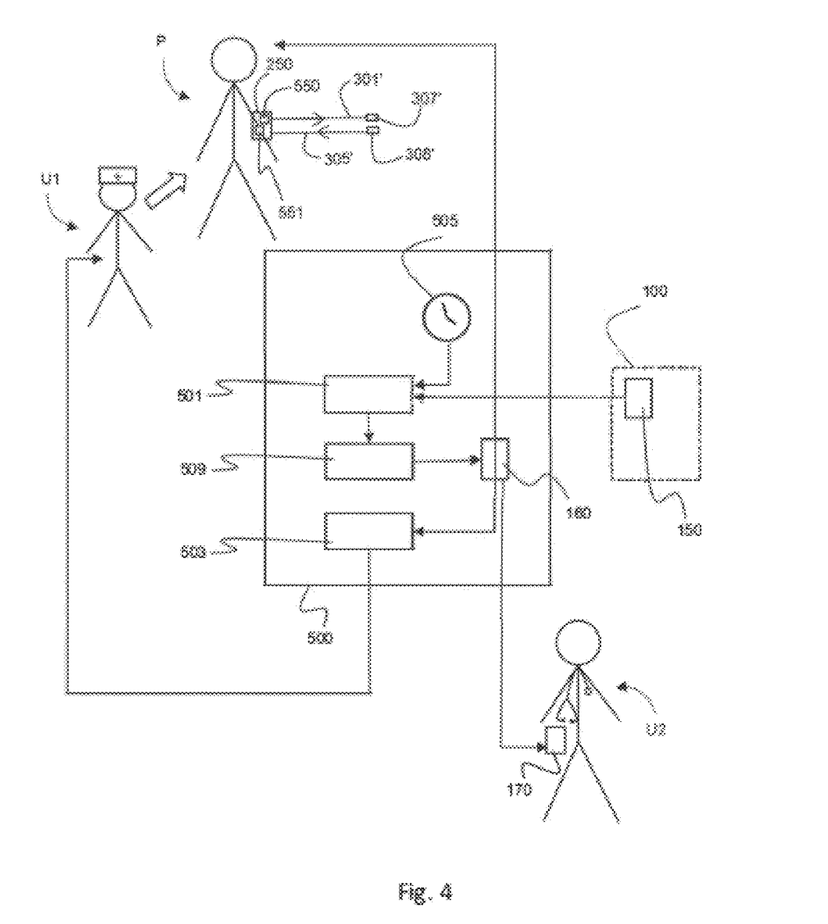
FIG. 4 shows a simplified representation of a medical set according to a third embodiment.

FIG. 4 shows a simplified representation of a medical set according to the present invention in a second embodiment. As in FIG. 2, the blood treatment apparatus 100 which is optionally encompassed by the set is only schematically outlined in FIG. 4.

The features of the user information device 500 and its devices described in FIG. 2 may also be undiminished implemented in the user information device 500 of FIG. 4.

In the embodiment of FIG. 4, the user information device 500 of the set comprises, respectively optionally, a determining device 501, an evaluating device 509, an input/output device 503, a time recording device 505 and/or a sending device 160.

The determining device 501 serves the user information device 500 to determine a suitable time point $t_P$ or time period $T_{max}$ for puncturing the vessel of the patient P. To this end, a plurality of designs and possible uses of the determining device 501 are again contemplated by the present invention. Some of these designs will be described in more detail with reference to FIG. 4.

In the embodiment of FIG. 4, the determining device 501 may be configured to determine, at an earlier time point t0, a time point $t_B$ in the future at which the blood treatment apparatus 100 is likely to be ready for the start of the blood treatment session planned for the patient P.

The time point $t_B$ may have been transmitted (directly or indirectly), preferably automatically, to the determining device 501 by the control device or closed-loop control device 150 of the blood treatment apparatus 100. Thus for example, with the beginning of the blood return by the end of the treatment session of the patient P-1 preceding the specific patient P, at the beginning of the priming of the blood tubing set intended for the treatment session of the patient P, etc., an indication is sent to the determining device 501 as to when the blood treatment apparatus 100 will be ready for the start of the blood treatment of patient P.

According to the present invention, it is optionally provided, in addition or alternatively, that the specification of the time point $t_B$ at which the blood treatment apparatus 100 will be ready for the start of the planned blood treatment of the patient P may also take place at time point t0 by (via) active manual input, for example by the user U2 at a receiver/sender 170 (not shown in FIG. 4).

The determining device 501 may be programmed to read in or import the time point $t_B$ thus transmitted or entered and transmit it to the evaluating device 509.

The evaluating device 509 serves the user information device 500 to generate information based on the time point $t_B$ determined as mentioned above and on the time period $T_{max}$ defined as being the maximum permissible, which relate to a suitable time point t1, at or after which it is reasonable to puncture the patient P taking well care about preventing blood clotting for the upcoming blood treatment. The time point t1 may subsequently be transmitted to the sending device 160.

Figure 5:
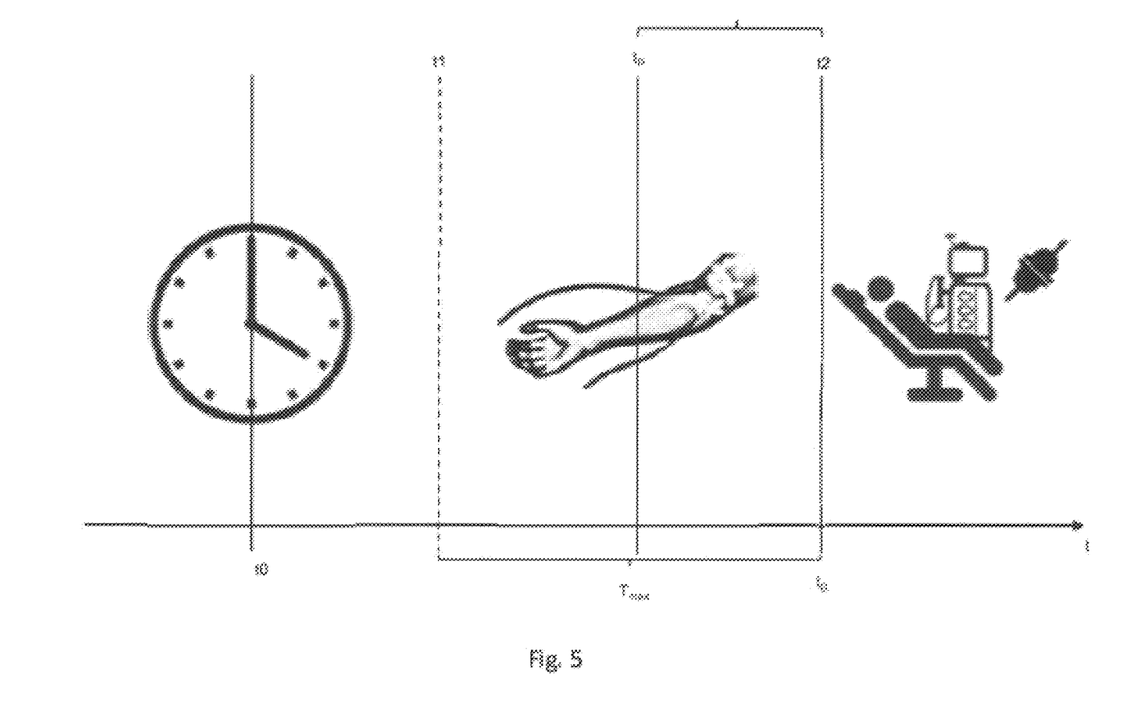
FIG. 5 shows a simplified representation of a sequence of a method according to a second embodiment.

For the time period $T_{max}$ which is defined as being the maximum permissible, the statements made in relation to FIG. 2 also apply. In the example of FIG. 5, reference is made to the end t2 and to the start t1 of the period $T_{max}$.

Starting from or based on the determined time point $t_B$, which in the embodiment shown in FIG. 5 is set equal to the end t2 of the time period $T_{max}$ ($t_B$=t2), the time point t1, i.e. the beginning of the time period $T_{max}$, may now be determined, e.g. calculated, by the evaluating device 509. From said time point t1, the vessel of patient P should be punctured so that later at the time point $t_B$ his blood treatment may be started using the blood treatment apparatus 100 without having to worry about blood clotting. For this purpose, the time point of the puncture $t_P$ is advantageously within the time period $T_{max}$, i.e. between the times t1 and t2 with a time period T as a distance to the time point $t_B$, wherein T≤Tmax applies.

The sending device 160 is configured to send the information at the time point t1 which it has received from the evaluating device 509 to devices provided for this purpose, which are intended to output said information. These devices may be, for example, the input/output device 503 of the user information device 500, for example a display, and/or the receiver/sender 170 of the user U1 or U2, for example his beeper, smartphone or tablet. Alternatively or additionally, such a device may be accessible by the patient P, for example as his smartphone.

FIG. 5 shows in a simplified representation the time or chronological sequence of the method according to the present invention in a second embodiment.

At time point t0, information about the status of the blood treatment apparatus 100 is transmitted from the control device or closed-loop control device 150 of the blood treatment apparatus 100 to the determining device 501, in particular information related to the time point $t_B$ in the future at which the blood treatment apparatus 100 may be started for the blood treatment of the patient P (see FIG. 4).

As explained in the description of FIG. 4, a time point t1 may be determined by the evaluating device 509, based on the time point $t_B$, which in this embodiment is set equal to the end t2 of a suitable time period T.

The time point t1 and each subsequent time point within the time period $T_{max}$, which is defined as being the maximum permissible, is suitable for puncturing the vessels of the patient P. A puncturing done after the specified time point t1 or within the specified time period $T_{max}$ may ensure that blood of the patient P does not clot in the cannulas and in the line sections 301', 305' during the waiting period for the start of the blood treatment of said patient P.

While the invention has been illustrated and described in detail in the drawings and foregoing description, such illustration and description are to be considered illustrative or exemplary and not restrictive. It will be understood that changes and modifications may be made by those of ordinary skill within the scope of the following claims. In particular, the present invention covers further embodiments with any combination of features from different embodiments described above and below. Additionally, statements made herein characterizing the invention refer to an embodiment of the invention and not necessarily all embodiments.

The terms used in the claims should be construed to have the broadest reasonable interpretation consistent with the foregoing description. For example, the use of the article "a" or "the" in introducing an element should not be interpreted as being exclusive of a plurality of elements. Likewise, the recitation of "or" should be interpreted as being inclusive, such that the recitation of "A or B" is not exclusive of "A and B," unless it is clear from the context or the foregoing description that only one of A and B is intended. Further, the recitation of "at least one of A, B and C" should be interpreted as one or more of a group of elements consisting of A, B and C, and should not be interpreted as requiring at least one of each of the listed elements A, B and C, regardless of whether A, B and C are related as categories or otherwise. Moreover, the recitation of "A, B and/or C" or "at least one of A, B or C" should be interpreted as including any singular entity from the listed elements, e.g., A, any subset from the listed elements, e.g., A and B, or the entire list of elements A, B and C.

The invention claimed is:

1. A system, comprising:
one or more processors; and
one or more memories having processor-executable instructions stored thereon;
wherein the processor-executable instructions, when executed by the one or more processors, facilitate performance of the following by the system:
determining a time point with regard to puncturing a vessel of a patient in preparation for treating the patient via the punctured vessel using a blood treatment apparatus;
determining whether an amount of time that has elapsed since the determined time point exceeds a maximum permissible time period between puncturing the vessel and starting a blood treatment provided via the punctured vessel; and
in response to determining that the amount of time that has elapsed since the determined time point exceeds the maximum permissible time period between puncturing the vessel and starting the blood treatment via the punctured vessel, blocking, at least temporarily, execution of at least one function of the blood treatment apparatus.

2. The system according to claim 1, further comprising:
the blood treatment apparatus, wherein the blood treatment apparatus comprises a control device configured to control the blood treatment for the patient.

3. The system according to claim 1, wherein the processor-executable instructions, when executed by the one or more processors, further facilitate performance of the following by the system:
transmitting data related to the determined time point and/or data related to the maximum permissible time period to a receiving device.

4. The system according to claim 3, wherein the receiving device is a mobile device.

5. The system according to claim 1, wherein the determined time point indicates a time point at which the vessel of the patient was punctured.

6. The system according to claim 1, wherein the determined time point corresponds to a future time point at which the blood treatment apparatus will be ready to start a new blood treatment and/or at which the patient is permitted to be connected to the blood treatment apparatus.

7. The system according to claim 1, wherein the determined time point corresponds to a suitable time point for puncturing the vessel of the patient.

8. The system according to claim 1, wherein the processor-executable instructions, when executed by the one or more processors, further facilitate performance of the following by the system:
determining a second time point which corresponds to an earliest possible time for puncturing the vessel of the patient.

9. The system according to claim 1, wherein the determined time point corresponds to a suitable time point for puncturing the vessel of the patient determined according to predetermined criteria, wherein the predetermined criteria comprises one or more of the following:
a history of the patient corresponding to an average amount of elapsed time between a respective time point at which the vessel of the patient was punctured and a respective time point at which the patient appeared at the blood treatment apparatus; or an actual start of treatment of a previous blood treatment session of the patient.

10. The system according to claim 1, wherein the determined time point is a time point at which the vessel of the patient was punctured, and determining the determined time point is based on receiving a user input.

11. The system according to claim 1, wherein the determined time point is a time point at which the blood treatment apparatus is ready to start a blood treatment session, and determining the determined time point is based on receiving a user input.

12. The system according to claim 1, wherein the determined time point is a time point at which the vessel of the patient was punctured, and determining the determined time point is performed automatically.

13. The system according to claim 1, wherein the processor-executable instructions, when executed by the one or more processors, further facilitate performance of the following by the system:

linking information on the determined time point with an identity of the patient.

14. The system according to claim 1, wherein the processor-executable instructions, when executed by the one or more processors, further facilitate performance of the following by the system:

capturing or realizing a QR code and/or biometric data.

15. The system according to claim 1, wherein the processor-executable instructions, when executed by the one or more processors, further facilitate performance of the following by the system:

anonymously assigning the determined time point to the patient.

16. The system according to claim 1, wherein the processor-executable instructions, when executed by the one or more processors, further facilitate performance of the following by the system:

authenticating a user of a device; and based on authenticating the user of the device, permitting data input or data manipulation.

17. The system according to claim 1, wherein the blood treatment apparatus is a dialysis apparatus, a hemodialysis apparatus, a hemofiltration apparatus or a hemodiafiltration apparatus.

18. The system according to claim 1, further comprising:

a pressure sensor configured to detect a pressure change associated with the patient being present on a stretcher or chair on which puncturing occurs;

wherein determining the time point is based on information from the pressure sensor.

19. The system according to claim 1, further comprising:

an optical sensor configured to detect the patient being present on a stretcher or chair on which puncturing occurs;

wherein determining the time point is based on information from the optical sensor.

20. A method, comprising:

determining, by a system, a time point with regard to puncturing a vessel of a patient in preparation for treating the patient via the punctured vessel using a blood treatment apparatus;

determining, by the system, whether an amount of time that has elapsed since the determined time point exceeds a maximum permissible time period between puncturing the vessel and starting a blood treatment provided via the punctured vessel; and in response to determining that the amount of time that has elapsed since the determined time point exceeds the maximum permissible time period between puncturing the vessel and starting the blood treatment via the punctured vessel, blocking, by the system, at least temporarily, execution of at least one function of the blood treatment apparatus.

21. One or more non-transitory computer-readable mediums having processor-executable instructions stored thereon, wherein the processor-executable instructions, when executed, facilitate:

determining a time point with regard to puncturing a vessel of a patient in preparation for treating the patient via the punctured vessel using a blood treatment apparatus;

determining whether an amount of time that has elapsed since the determined time point exceeds a maximum permissible time period between puncturing the vessel and starting a blood treatment provided via the punctured vessel; and in response to determining that the amount of time that has elapsed since the determined time point exceeds the maximum permissible time period between puncturing the vessel and starting the blood treatment via the punctured vessel, blocking, at least temporarily, execution of at least one function of the blood treatment apparatus.

* * * * *